United States Patent [19]
Feil

[11] Patent Number: 4,722,904
[45] Date of Patent: Feb. 2, 1988

[54] THERMODYNAMICALLY-STABLE AQUEOUS PERFLUOROCARBON MICROEMULSION USEFUL AS BLOOD GAS CONTROL OR CALIBRATOR

[75] Inventor: Marvin C. Feil, Brookline, Mass.

[73] Assignee: Fisher Scientific Company, Pittsburgh, Pa.

[21] Appl. No.: 943,373

[22] Filed: Dec. 18, 1986

[51] Int. Cl.$^4$ .................... G01N 31/00; A01N 29/04
[52] U.S. Cl. ......................... 436/11; 436/18; 252/312
[58] Field of Search ..................... 436/8–18; 252/408.1, 312, 186.32; 424/325, 339, 342, 350, 352

[56] References Cited

U.S. PATENT DOCUMENTS

| | | | |
|---|---|---|---|
| 3,911,138 | 10/1975 | Clark | 436/11 |
| 4,116,336 | 9/1978 | Sørensen et al. | 436/11 |
| 4,146,499 | 3/1979 | Rosano | 252/186.32 |
| 4,151,108 | 4/1979 | Sørensen et al. | 436/11 |
| 4,163,734 | 8/1979 | Sørensen et al. | 436/11 |
| 4,299,728 | 11/1981 | Cormier et al. | 436/11 |
| 4,369,127 | 1/1983 | Cormier et al. | 436/11 |

Primary Examiner—Deborah L. Kyle
Assistant Examiner—T. J. Wallen
Attorney, Agent, or Firm—Alan M. Doernberg

[57] ABSTRACT

The present invention relates to aqueous perfluorocarbon emulsions and particularly microemulsions, and to their use as blood gas controls and calibrators.

19 Claims, 11 Drawing Figures

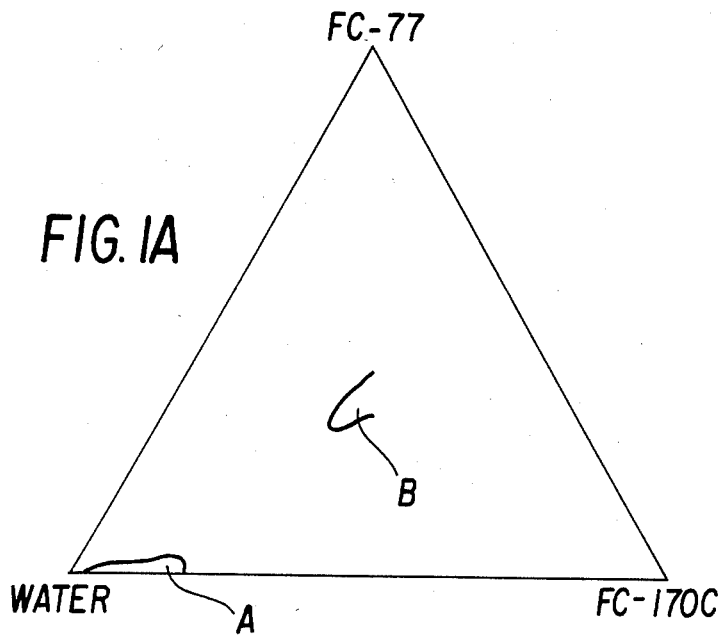
FIG. IA
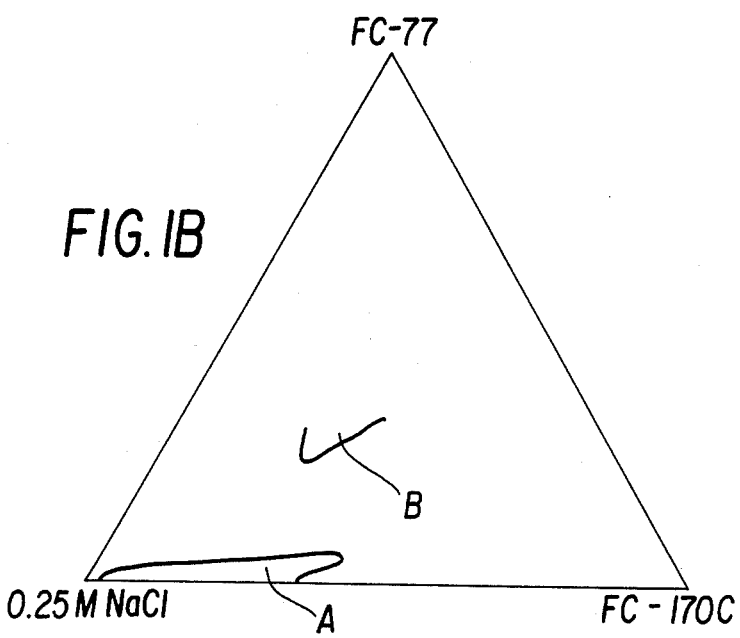
FIG. IB

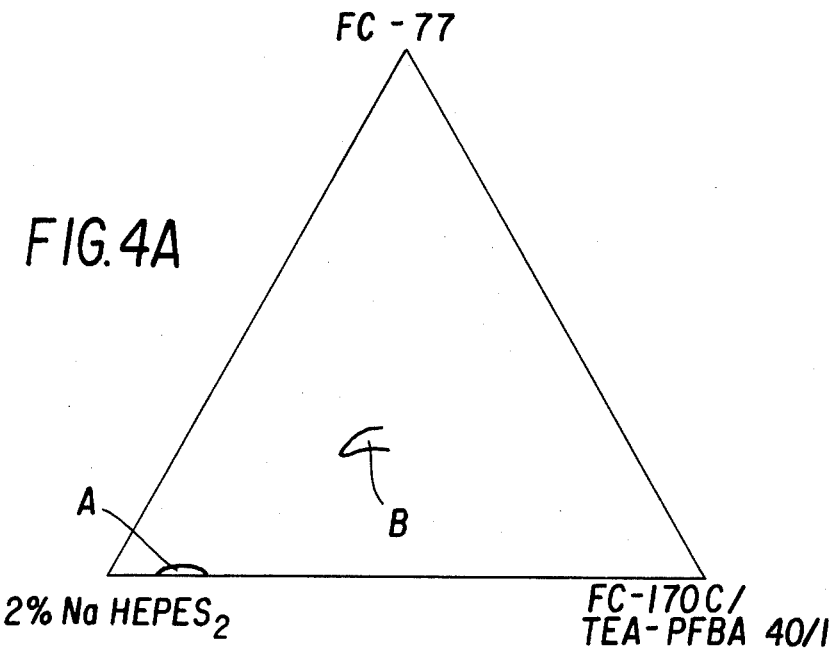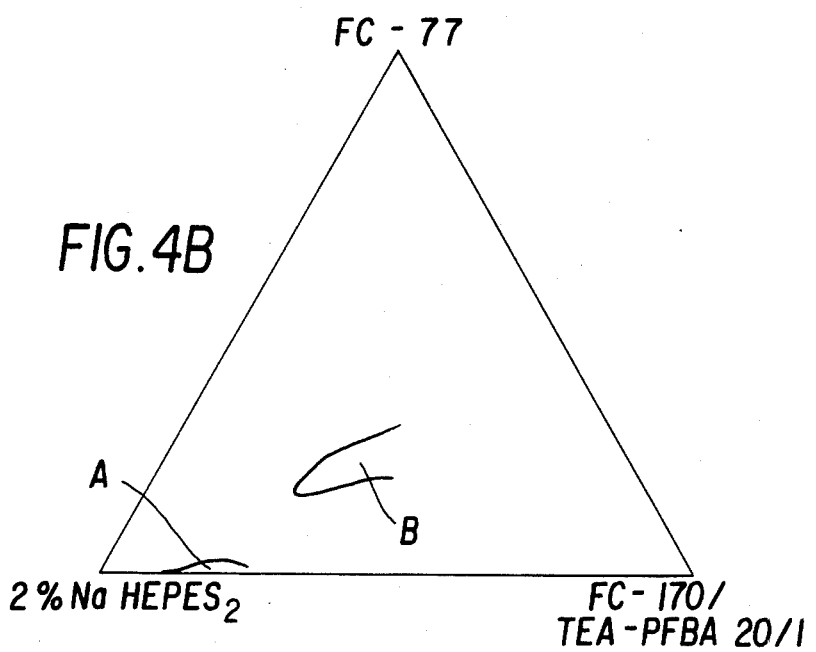

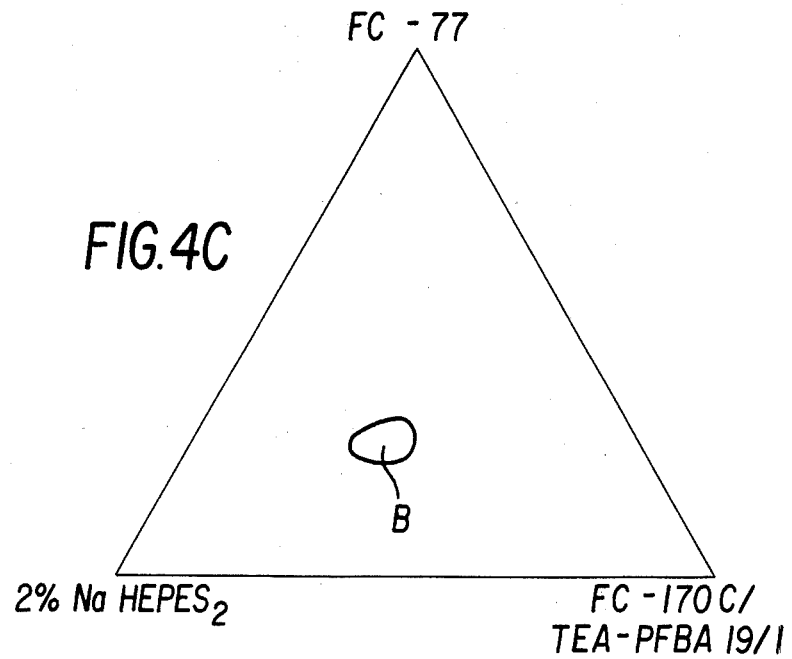
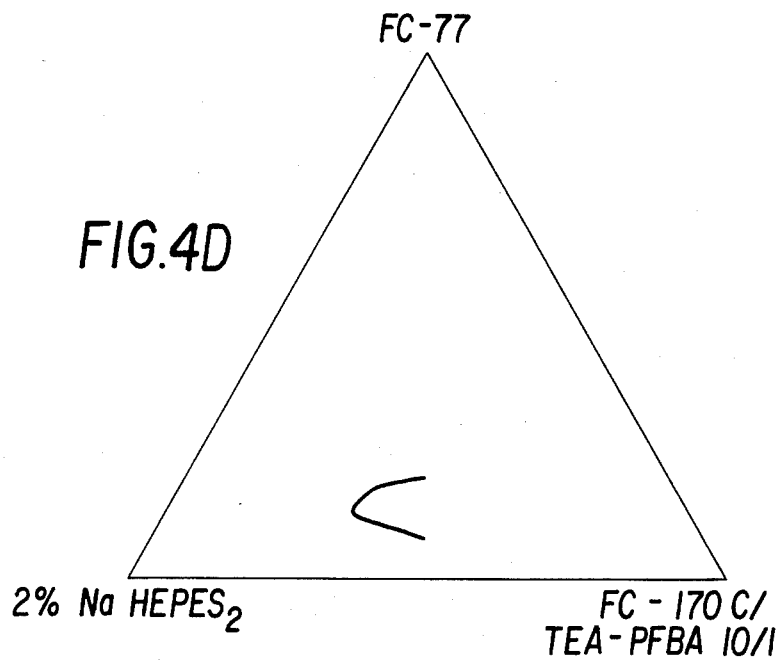

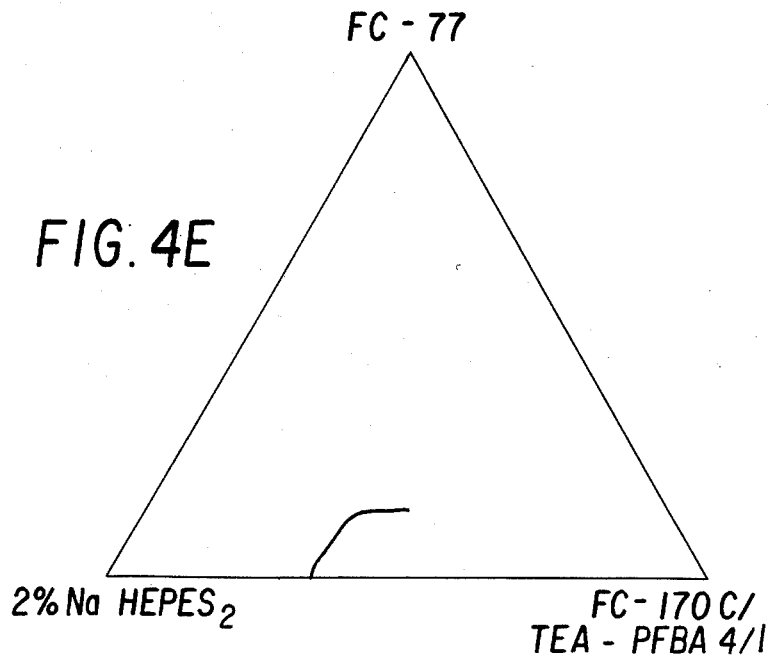

1

THERMODYNAMICALLY-STABLE AQUEOUS PERFLUOROCARBON MICROEMULSION USEFUL AS BLOOD GAS CONTROL OR CALIBRATOR

BACKGROUND OF THE INVENTION

Aqueous perfluorocarbon emulsions have been explored as blood substitutes, especially for transfusions. One goal in such formulations has been to employ a perfluorocarbon of greatest oxygen solubility to the maximum concentration feasible while maintaining a perflurocarbon-in-water emulsion. Emulsifiers (surfactants) for such applications are reviewed in I.R. Schmolka, "Artificial Blood Emulsifiers," *Federation Proceedings*, vol. 34, pp. 1449–1453 (1975). There, various desired properties of the non-ionic emulsifiers are set forth, including non-toxicity. The paper also discusses the distinctions between a microemulsion and a macroemulsion (droplet size under 0.1 microns versus 0.1 to 2 microns). The paper indicates that when two surfactants are used, then rather than mixing the two together, one should dissolve the water-soluble surfactant in the aqueous phase and the water-insoluble surfactant in the oil (perfluorocarbon) phase. A similar teaching is contained in U.S. Pat. No. 4,146,499 to Rosano (1979), which emphasizes mixing order (the water-insoluble surfactant and then the water-soluble surfactant) and discounts as incorrect the pre-1972 belief that microemulsions should be thought of as thermodynamically stable systems. It is reasonable to infer from Rosano that his clear microemulsions are metastable rather than thermodynamically stable, being dependent for their formation upon adding ingredients in a particular order (creating a specified "transient" condition). When such metastable microemulsions are broken (generally by heating too hot or freezing), they would not reform upon returning to room temperature, even with mild agitation. In some cases, no amount of agitation can restore such metastable emulsions once broken.

Perfluorocarbon-in-water emulsions have been disclosed for use as blood gas controls and calibrators. See U.S. Pat. Nos. 4,151,108 and 4,163,734 to Sorenson and U.S. Pat. Nos. 4,299,728 and 4,369,127 to Cormier et al. In such cases, the aqueous phase is buffered for an assayable pH value and is equilibrated with oxygen-containing gases for an assayable $pO_2$ value. A blood gas control also has an assayable $pCO_2$ value which is obtained by one or more of:
(a) equilibration with $CO_2$-containing gases,
(b) addition of a bicarbonate source, and
(c) addition of a carbonate source (some pH adjustment being sometimes employed for some of these, e.g., NaOH added when $CO_2$-containing gases are the sole manner of introducing $CO_2$).

The fluorocarbon is chosen as one with high oxygen solubility so that the overall emulsion will dissolve more oxygen at a given temperature than water does (leading to an "oxygen-buffering" effect in that the $pO_2$ value is deflected less from the assayed value under circumstances such as brief contact with air). FC-77 and FC-43 are used in admixture in the Cormier et al patents.

Commercial blood gas controls, including those based upon the Cormier et al patents, are macroemulsions that are stable (against breaking) for extended periods (at least two years, but not indefinitely), but have a tendancy within a few days to cream, i.e., form a layer enriched in the discontinuous fluorocarbon phase (analogous to the creaming of the discontinuous oily phase in non-homogenized milk but tending to sediment since the fluorocarbon phase is denser than the aqueous phase). The creamed composition can be restored by manual shaking. If, however, the macroemulsions are broken (e.g., because of temperature either much higher or lower than the desired range), they cannot be restored except by vigorous agitation (as by reintroduction of the mixture into a homogenizer) which cannot be accomplished easily for sealed ampules of a blood gas control having assayed values which are desired to be maintained.

BRIEF DESCRIPTION OF THE INVENTION

The present invention is based upon selecting two surfactants for perfluorocarbon-in-water microemulsions in such a way that a microemulsion which is thermodynamically stable can be formed. The surfactants are selected in the opposite order from that set forth in U.S. Pat. No. 4,146,499 to Rosano: the water-soluble primary surfactant is selected first. The resultant microemulsions are thermodynamically stable and therefore can be reformed from systems in which the microemulsion has been broken thermally. Because the microemulsions are thermodynamically stable, the order of addition of ingredients is not critical and the two surfactants can be admixed with each other. Three beneficial properties result: (a) the compositions do not cream and therefore are more useful as blood gas controls without shaking, (b) even if the emulsion is broken by temperature stress, it can be restored by mild agitation (even shaking a sealed ampule) and (c) the emulsion has the improved appearance of a clear liquid rather than a milky liquid. These benefits have particular application for use as a calibrator as well as a control since a calibrator should remain homogeneous over a prolonged period while individual aliquots are taken into the instrument and it is not desireable to periodically shake a calibrator to retain homogeneity.

Thus the present invention provides a blood gas control or calibrator having an assayed value of $pO_2$ and being an emulsion of a perfluorocarbon phase dispersed in a pH buffered aqueous phase;
characterized by the emulsion being a microemulsion which is thermodynamically stable at room temperature, contains at least 10 weight percent of a perfluorocarbon of high oxygen solubility and contains two surfactants, the primary surfactant being non-ionic and water-soluble, and the secondary surfactant being hydrotropic and present in an amount sufficient to disorder any water-primary surfactant gels.

The present invention also provides a thermodynamically-stable aqueous microemulsion comprising:
(a) a continuous pH buffered aqueous phase,
(b) a perfluorocarbon of high oxygen solubility as 10–30 weight percent of the emulsion,
(c) a primary surfactant which is non-ionic and water soluble, the perfluorocarbon-water-primary surfactant phase diagram showing both a micellular solution region and a microemulsion region, and
(d) a co-surfactant capable of disordering any gels formed by the aqueous phase and the primary surfactant or by the aqueous phase, primary surfactant, co-surfactant system;
the microemulsion being stable for at least three months at room temperature and being restored with only gentle mixing upon returning to room temperature after either being heated or frozen.

BRIEF DESCRIPTION OF THE DRAWING

FIG. 1A shows a phase diagram of the FC-77/water/FC-170C system showing separate micellar region A and microemulsion region B because of the absence of cosurfactant.

FIG. 1B shows a phase diagram similar to FIG. 1A of the FC-77/0.25M aqueous NaCl/FC-170C system having similar regions A and B.

FIG. 4A shows a phase diagram of the FC-77/(1% HEPES, 1% NaHEPES, 98% water)/(FC-170C/TEA-PFBA) (40/1) system with separate micellar region A and microemulsion region B.

FIG. 4B is a phase diagram similar to FIG. 4A in which the altered FC-170C/TEA-PFBA ratio (20/1 instead of 40/1) causes the microemulsion region B to come closer to, but not intersect, the micellar region A.

FIG. 4C is a phase diagram similar to 4A in which the altered FC-170C/TEA-PFBA ratio (19/1 instead of 40/1) has caused the separate micellular region to disappear and only microemulsion region B to be present, and to include high (20-25%) FC-77 contents.

FIGS. 4D and 4E show phase diagrams similar to FIG. 4C, except that the altered FC-170C/TEA-PFBA ratios (10/1 and 4/1, respectively, instead of 19/1) cause the microemulsion region to have somewhat lower FC-77 contents, but still prevent the existence of a micellar region.

DETAILED DESCRIPTION

Figure 2:
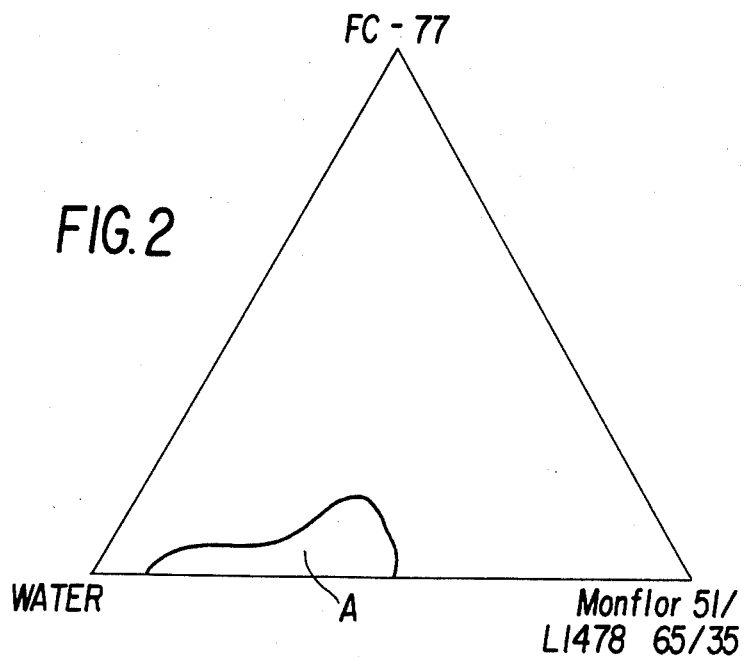
FIG. 2 shows a phase diagram of the FC-77/water/-(Monoflor/L1478) (65/35) system having a broadened micellar region A.

The four major ingredients of the microemulsion of the present invention are the aqueous phase, perfluorocarbon, primary surfactant and secondary surfactant (co-surfactant). The aqueous phase contains, besides water, at least a pH buffer system, which may be inorganic (e.g., various mixtures of phosphate ions such as $HPO_4^{--}$ and $H_2PO_4^{-}$) or organic (such as HEPES or Tris). Expecially when the microemulsion is used as a blood gas control, the buffer system's components are provided in proportions giving a final measured pH at desired levels (e.g., pH 7.6, 7.4 and 7.2 for levels I, II and III). Organic buffer systems are preferred to avoid microbial growth and, in some cases, to avoid excessive ionic strengths which might interfere with certain electrodes in a blood gas instrument. Other ingredients that are commonly provided in the aqueous phase include preservatives and coloring agents (see the Cormier et al patents).

The perfluorocarbon should be one having a high oxygen solubility at room temperature. R. D. Danielson, "Fluoro Ethers And Amines", vol. 10 pp. 874–881, Kirk-Othmer, *Encyclopedia of Chemical Technology* (3d Ed. 1980), describes a class of materials as perfluorinated inert fluids comprising perfluoroaliphatic ethers, perfluoroalkyl tertiary amines and perfluoroalkanes. Many of these perfluorinated inert fluids are known to be liquid at room temperature and to have a solubility for oxygen considerably higher than does water (see Table 3 on page 877 of Danielson).

Among the best perfluorocarbons is FC-77 (a product of 3M Company and described as a mixture of perfluoroalkanes and perfluorocylic ethers) (see Table I of the Cormier et al patents). Other suitable perfluorocarbons (also given by 3M's designations) are FC-72, FC-88, FC-104 and FC-75. Mixtures of these perfluorocarbons having high oxygen solubility with each other are also suitable. Since all of these products are mutually miscible, any such combinations can be made. Somewhat less preferred are mixtures of the above perfluorocarbons with other perfluorocarbons having lower oxygen solubility, such as FC-43 (perfluorotributylamine). FC-43 admixed with FC-77 shows reduced oxygen solubility compared to FC-77 alone (see Table I of the Cormier et al patents), but was used therein because the mixture was easier to formulate into metastable emulsions. Other perfluorocarbons having oxygen solubility less than that of FC-104 or FC-75, but greater than that of FC-43, can be used as secondary perfluorocarbons; e.g., FC-40 or FC-48.

In addition to having a perfluorocarbon of high oxygen solubility in the microemulsion, it is desirable to have a high proportion of such perfluorocarbon: at least 10 weight percent, preferably at least 15 weight percent and more preferably at least 20 weight percent, especially of the preferred FC-77. With microemulsions having 20–25 weight percent FC-77, greater oxygen buffering capacity can be achieved compared to the 15% FC-77 and 5% FC-43 composition described in U.S. Pat. No. 4,299,728. The 20% FC-77 described in U.S. Pat. No. 4,299,728, while of similar high oxygen buffering capacity, formed emulsions whose stability was significantly less, making it unacceptable for commercial use.

The primary surfactant should be a water-soluble non-ionic surfactant. It should be chosen for a particular perfluorocarbon or perfluorocarbon mixture as one that will, for the three-ingredient system of:
water
perfluorocarbon
primary surfactant
or the three-ingredient systems of:
pH buffered aqueous phase
perfluorocarbon
primary surfactant
show two distinct regions (as in FIGS. 1A and 1B):
(1) a water-primary surfactant micellar solution phase (in which the perfluorocarbon may show only very limited solubility) (A in FIG. 1A), and
(2) a microemulsion phase with significant amounts of perfluorocarbon (at least 10 weight percent, preferably at least 15 weight percent, more preferably at least 20 weight percent) (B in FIG. 1).

Surfactant FC-170C (from 3M and apparently containing as active ingredient FC-170 described on page 1451 of the Schmolka article) has been found to be a suitable primary surfactant for FC-77 as the perfluorocarbon. FC-170C is described by the manufacturer as a perfluoroalkane polyoxyethylene ethanol and thus can be schematically shown as

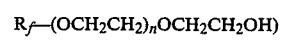

where $R_f$ is perfluoroalkyl.

It should be noted that the first formulation proposed in U.S. Pat. No. 4,299,728 (having 15% FC-70 and 5% FC-43) employed Zonyl FSN (a Dupont product) which is also a perfluoroalkane polyoxyethylene ethanol, but which has a higher cloud point (caused by a smaller $R_f$ group and/or a larger value for n) than FC-170C. For the present invention (wherein a co-surfactant is to be present as well), primary surfactants having a lower cloud point (in the absence of the co-surfactant) are preferred.

Monflor 51 (a product of ICI) is proposed at col. 4 of U.S. Pat. No. 4,299,728 as a surfactant for fluorocarbon-in-water emulsions of FC-77, and indicated to be a polymer of 20–25 polyethyleneoxides with 1–4 tetrafluoroethylene groups on each end, such that it can be schematically shown as

$$R_f-(OCH_2CH_2)_mOCH_2CH_2O-R_f$$

with $R_f$ having 2–8 carbons and m being 19–24. It has been found that the system FC-77/Monflor 51/water does not have the desired two regions. When Monflor 51 was blended with L1478 (a product previously available from 3M Company) some broadening of the micellar solution phase was seen (see FIG. 2), but no microemulsion region was seen. A similar broadening of the micellular region was also seen with other ratios of Monflor 51 with L1478, FC-77 and either water or 0.5M NaCl or 1.0M NaCl.

Thus, although Monflor 51 and FC-170C appear to be structurally similar, routine experimentation (such as that described herein) would be required to determine which is suitable for a particular perfluorocarbon. In simmilar fashion, other water-soluble non-ionic surfactants can be screened for any particular perfluorocarbon or mixture of perfluorocarbons.

Examples of the types of water-soluble non-ionic surfactants that could be screened for use in composition with any particular perfluorocarbon are (1) various fluorinated nonionic surfactants (including the above two classes)
(2) non-fluorinated non-ionic surfactants having ethylene oxide groups such as those defined structurally as poly ethylene glycol alkylaryl ethers and poly ethylene glycol polypropylene glycol block co-polymers).

Once the water-soluble primary surfactant is chosen, a secondary surfactant is next selected by routine experimentation. The secondary surfactant should be hydrotropic (generally of shorter chain length than the primary surfactant). Preferred are the highly fluorinated surfactants of 3–6 carbons, and especially the perfluorocarboxylic acids ($R_f$COOH), perfluorocarboxylates ($R_f$COO$^-$) and perfluoroalcohols ($R_f$CH$_2$CH$_2$OH and $R_f$CF$_2$OH). The first two classes are generally used in combination in that a perfluorocarboxylic acid will either be partially neutralized (e.g., with a tertiary amine such as triethanolamine) before introduction (as exemplified below), or will be so neutralized after the emulsion is formed by the pH buffer system in the aqueous phase. The advantage of prior neutralization is to avoid shifts of pH of the aqueous phase.

The function of the co-surfactant is to disorder any gels of lamellar or hexagonal cylindrical array structure (liquid crystals) that might otherwise form, either by the combination of water with primary surfactant or (in some cases) by water plus primary surfactant plus secondary surfactant. The region in FIGS. 1A and 1B between the micellar solution region A and the microemulsion region B contains such gels. It should be apparent that a microemulsion containing primary surfactant alone would be prone to such gels forming (e.g. upon large temperature changes) and be too stable for the system to return to solely a microemulsion (e.g., by returning to room temperature).

Figure 3A:
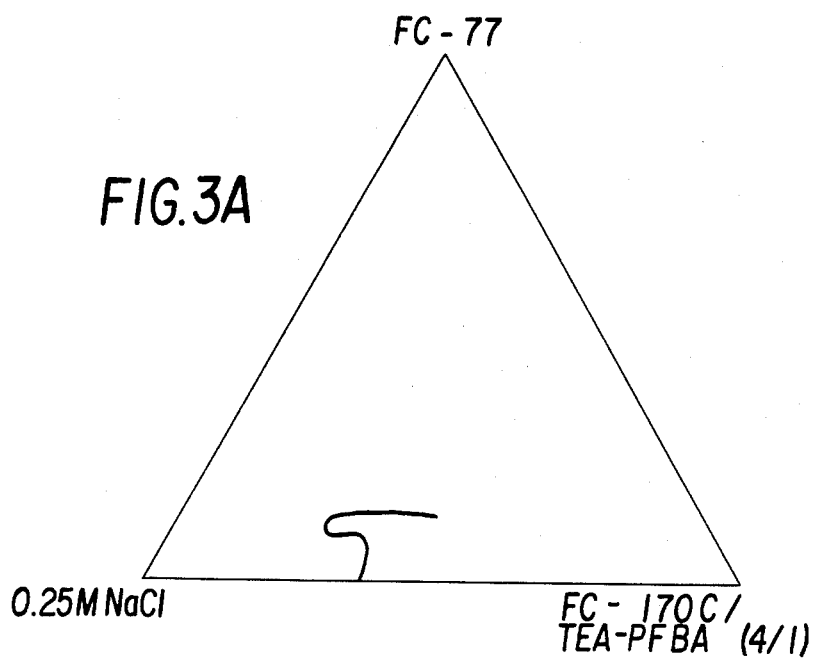
FIG. 3A shows a phase diagram of the FC-77/0.25M NaCl/(FC-170C/TEA-PFBA) (4/1) system having the desired microemulsion region of high FC-77 content.
Figure 3B:
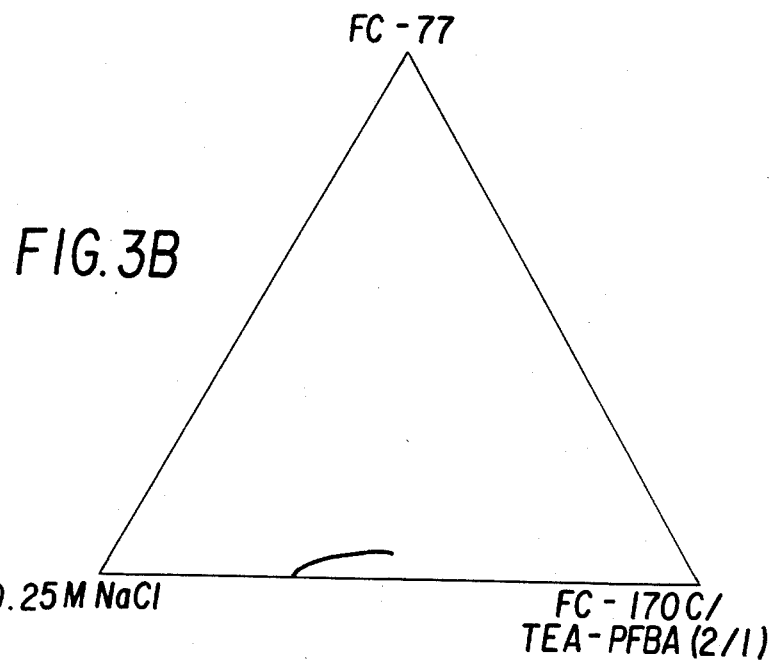
FIGS. 3B and 3C show similar phase diagrams to tha shown in FIG. 3A, except that the altered ratio of FC 170-C/TEA-PFBA of 2/1 and 1/1, respectively, lowers the peak FC-77 content of the microemulsion region.
Figure 3C:
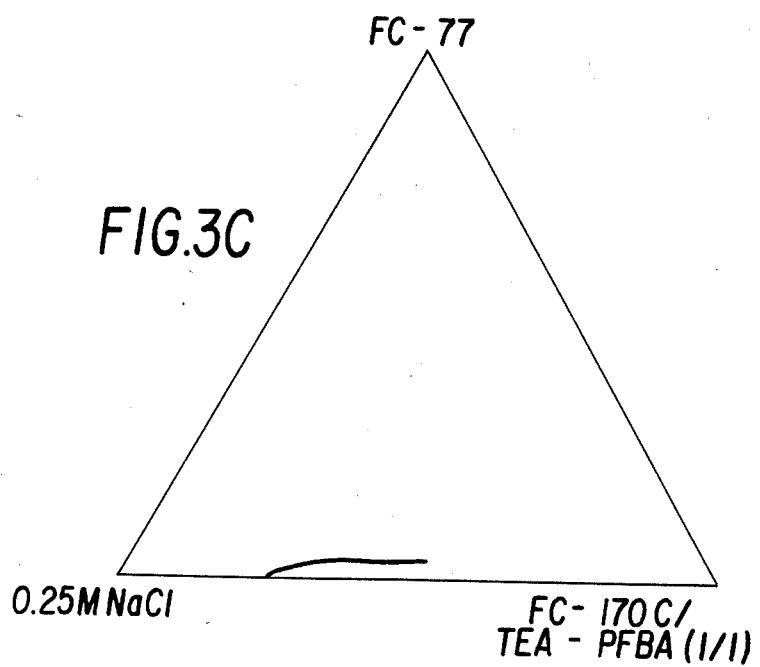

Since the present formulations are desired to be thermodynamically stable (and thus not dependent upon the order of addition) suitable hydrotropes can be screened by mixing them in various proprtions with the primary sufactant. Thus, as seen in FIGS. 3A, 3B and 3C, 4/1, 2/1 and 1/1 mixtures of FC-170C with triethanolamine-neutralized perfluorobutyric acid (TEA-PFBA) each yielded phase diagrams (with 0.25M NaCl and FC-77) with a microemulsion region continuous with the micellular solution region (FIGS. 3A, 3B and 3C, respectively). For this particular co-surfactant, the 4/1 mixture (FIG. 3A) is preferable because a larger proportion of FC-77 (about 20%) could be used and still achieve a microemulsion. When the 0.25M NaCl was replaced by 2% HEPES buffer (FIGS. 4A–4D), ratios of FC-170C to PFBA of 40/1 or 20/1 gave separate regions A and B (FIGS. 4A and 4B), but 19/1, 10/1 or 4/1 gave continuous regions (with 19/1 having the highest potential FC-77 content). The exemplary formulation (illustrated below) employs a 20/1 weight ratio FC-170C to PFBA, even though that mixture did not totally give a continuous region (FIG. 4B) because of the advantage of higher FC-77 content compared to the combination in FIG. 3A.

In similar fashion, once the perfluorocarbon, primary surfactant and aqueous phase have been selected, one can select the identity and proportion of co-surfactant by similar routine experimentation. It should be noted that the identity of co-surfactant (PFBA) was selected at high proportions of co-surfactant (20% or more of the primary sufactant plus co-surfactant), and then the amount of co-surfactant was determined by reduction to various levels (under 2.5% in FIG. 4A, under 5% in FIG. 4B, 5% in FIG. 4C and under 10% in FIG. 4D).

While the above description has been phrased in terms of a single primary surfactant (which is likely to be purchased as a mixture of chemical compounds) and a single co-surfactant, it is also contemplated to use more than one of either or both. It is also contemplated to use additives to lower the density of the microemulsion, e.g., silicone oil (for example, the DC200 Fluid having a specific gravity at 25° C. less than or equal to 0.90 from Dow Corning—a dimethyl siloxane polymer mixture). Such additives could be mixed with the perfluorocarbon separately or added at any stage of the process of mixing various ingredients. While the present microemulsions are insensitive to the order of addition, it is generally convenient to prepare these liquids:

(1) perfluorocarbon
(2) aqueous phase (including pH buffers, preservatives, dyes and salts), and
(3) surfactants (with the co-sufactant either neutralized separately, neutralized after mixing with the primary sufactant or not neutralized prior to admixture with the aqueous phase).

As indicated above, the perfluorocarbon is preferably at least 10 weight percent (e.g., 20–25%) of the formulation. From FIGS. 4B and 4C it should be apparent that the ratio of aqueous phase to total surfactants should be that giving the microemulsion region permitting the most perfluorocarbon (slightly left of center in each of FIGS. 4B and 4C such that 41% aqueous buffer and 36% surfactant is used in the exemplary formulation).

EXAMPLE 1

Generation Oo Phase Diagrams

Various ternary phase diagrams were generated by preparing several mixtures of three liquids (FC-77, water or aqueous buffer and surfactant or surfactant mixture) and gradually adding one component or another until a phase change was observed. Several of the phase diagrams prepared are illustrated in the Figures. For each case, boundaries between regions on the chart were established by adding a component and then observing the turbidity of the sample.

The three liquids for each Figure were as follows:

TABLE I

FC-77 Ternary Mixtures

| FIG. | Aqueous | Surfactant |
|---|---|---|
| 1A | Water | FC-170c |
| 1B | 0.25 M NaCl | FC-170c |
| 2 | Water | Monflor 51/L 1478 (65/35) |
| 3A | 0.25 M NaCl | FC-170C/TEA—PFBA (4/1) |
| 3B | 0.25 M NaCl | FC-170C/TEA—PFBA (2/1) |
| 3C | 0.25 M NaCl | FC-170-C/TEA—PFBA (1/1) |
| 4A | 1% NaHEPES, 1% HEPES | FC-170-C/TEA—PFBA (40/1) |
| 4B | 1% NaHEPES, 1% HEPES | FC-C/TEA—PFBA (20/1) |
| 4C | 1% NaHEPES, 1% HEPES | FC-170 C/TEA—PFBA (19/1) |
| 4D | 1% NaHEPES, 1% HEPES | FC-170 C/TEA—PFBA (10/1) |
| 4E | 1% NaHEPES, 1% HEPES | FC-170 C/TEA—PFBA (4/1) |

PFBA - perfluorobutyric acid neutralized to pH 7.0 in FIGS. 3A, 3B, 3C, 4A, 4C and 4D, to pH 6.9 in FIG. 4B and to pH 6.65 in FIG. 4E
1% NaHEPES, 1% HEPES - a mixture of one part by weight N—2-Hydroxyethyl Piperazine - N'—2-Ethane Sulfonic Acid, one part by weight of its monosodium salt and 98 parts by weight water.

EXAMPLE 2

Exemplary Formulation Of Microemulsion

Mixtures were prepared at various scales of these liquids:

(A) 5 g HEPES, 5 g NaHEPES, one liter water. pH was then adjusted to various desired levels (e.g. pH 7.2, 7.4 or 7.6 used in blood gas controls) by adding HEPES or NaHEPES until the desired pH value as measured on a blood gas instrument was achieved;

(B) 10 g perfluorobutyric acid plus 200 g FC-170C. Triethanolamine was then added to the mixture in increments and, after each increment, 1 ml of the solution was mixed with 2 ml water. The pH was then checked on the aliquot with a pH meter. Triethanolamine was added until pH 7.4 was reached.

(C) FC-77 as purchased from 3M. Into a two liter vessel were combined 410 g of A, 230 g of C and 360 g of B. Upon gentle mixing (hand shaking the vessel) a microemulsion formed.

One aliquot of such microemulsion has been maintained at room temperature in a 10 ml fused vial for 24 months. Another aliquot has been cooled to −20° C., where the emulsion broke as the water solidified. Upon warming to room temperature and gentle mixing, the clear microemulsion reformed. Another aliquot has been heated to 80° C., where the emulsion broke into two phases. Again upon cooling to room temperature and gentle swirling, the clear microemulsion reformed.

EXAMPLE 3

Demonstration As A Blood Gas Control

The buffer MOPS was added to water at a concentration of 74 mmol per liter (0.030M final concentration) as solution A. Solution B contained 5 g of PFBA, 100 g of FC 170C and 5 g of triethanolamine. Solution A, Solution B and FC-77 were then mixed at a 41:36:23 weight ratio and shaken to form a clear microemulsion. The microemulsion was then tonometered for 15 minutes with a gas mixture 10.6% $CO_2$, 89.4% $N_2$ (no oxygen) at a barometric pressure of 756 torr. When a sample of the tonometered microemulsion who analyzed on an IL Model 1312 Blood Gas Instrument, it showed a pH of 6.860 (6.948 before tonometry), a $pCO_2$ of 73.5 (compared to a theoretical value of 74.0) and a $pO_2$ of 4 to 5. This very low $pO_2$ value after tonometry in an oxygen-free gas mixture demonstrates effective oxygen buffering capacity.

EXAMPLE 4

Demonstration As A Blood Gas Control

To water was added 62 mmol per liter (0.025M final concentration) $Na_2HEPES$ and 12 mmol per liter (0.005M final concentration) HEPES as solution A. Solution B contained 5 g of PFBA, 100 g of FC-170C and 5 g of triethanolamine. Solution A, solution B and FC-77 were then mixed at a 41:36:23 weight ratio and shaken to form a clear microemulsion. Before tonometry, the microemulsion showed a pH of 7.4–7.5 (7.436 on a blood gas instrument). The microemulsion was then tonometered for 15 minutes with a gas mixture of 3.57% $CO_2$, 21.89% $O_2$ and the balance nitrogen at a barometric pressure of 751 torr. When a sample of the tonometered microemulsion was analyzed on an IL Model 1312 Blood Gas Instrument, it showed a pH of 7.372, a $pCO_2$ of 26 (compared to a theoretical value of 25.13) and a $pO_2$ of 152 (compared to a theoretical value of 154).

What is claimed is:

1. A blood gas control or calibrator having an assayed value of $pO_2$ and being an emulsion of a perfluorocarbon phase dispersed in a buffered aqueous phase;
   characterized by the emulsion being a microemulsion which is thermodynamically stable at room temperature, contains at least 10 weight percent of a perfluorocarbon of high oxygen solubility and contains two surfactants, the primary surfactant being non-ionic and water soluble and the secondary surfactant being hydrotropic and present in an amount sufficient to disorder any water-primary surfactant gels.

2. The blood gas control of claim 1 wherein the perfluorocarbon major constituent is selected from the group consisting of FC-77, FC-72, FC-88, FC-104, FC-75, mixtures thereof and mixtures thereof with other perfluorocarbons wherein at least one of the above-listed perfluorocarbons is the major constituent.

3. The blood gas control or calibrator of claim 2 wherein the perfluorocarbon is FC-77.

4. The blood gas control or calibrator of claim 3 containing at least 15 weight percent FC-77.

5. The blood gas control or calibrator of claim 4 containing 20 to 25 weight percent FC-77.

6. The blood gas control or calibrator of claim 1 containing at least 15 weight percent of FC-77, FC-72, FC-88, FC-104, FC-75 or mixtures thereof.

7. The blood gas control or calibrator of claim 1 wherein the perfluorocarbon is FC-77 and the primary surfactant is a perfluoroalkyl polyoxyethylene ethanol.

8. The blood gas control or calibrator of claim 7 wherein the secondary surfactant is a fluorinated hydrotropic co-surfactant of 3-6 carbons.

9. The blood gas control or calibrator of claim 8 wherein the fluorinated hydrotropic co-surfactant is a carboxylic acid, carboxylate or alcohol of 3-6 carbons.

10. The blood gas control or calibrator of claim 9 wherein the fluorinated hydrotropic co-surfactant is perfluorobutyrate.

11. The blood gas control or calibrator of claim 9 wherein FC-77 is present as at least 20 weight percent of the microemulsion.

12. A thermodynamically-stable aqueous microemulsion comprising:
   (a) a continuous pH buffered aqueous phase,
   (b) a perfluorocarbon of high oxygen solubility as 10-30 weight percent of the emulsion,
   (c) a primary surfactant which is non-ionic and water soluble, the perfluorocarbon-water-primary sufactant phase diagram showing both a micellular solution region and a microemulsion region, and
   (d) a co-surfactant capable of disordering any gels formed by the aqueous phase and the primary surfactant or by the aqueous phase, primary surfactant, co-sufactant system;

the microemulsion being stable for at least three months at room temperature and being restored with only gentle mixing upon returning to room temperature after either being heated or frozen.

13. The thermodynamically-stable aqueous microemulsion of claim 12 wherein the perfluorocarbon is selected from the group consisting of FC-77, FC-72, FC-88, FC-104, FC-75, mixtures thereof and mixtures thereof with other perfluorocarbons wherein at least one of the above-listed perfluorocarbons is the major constituent.

14. The thermodynamically-stable aqueous microemulsion of claim 13 wherein the perfluorocarbon is FC-77.

15. The thermodynamically stable aqueous microemulsion of claim 14 being at least 15 weight percent FC-77.

16. The thermodynamically stable aqueous microemulsion of claim 14 being from 20-25 weight percent FC-77.

17. The thermodynamically-stable aqueous microemulsion of claim 16 wherein the primary sufactant is a perfluoroalkyl polyoxyethylene ethanol.

18. The thermodynamically-stable aqueous microemulsion of claim 17 wherein the co-surfactant is a fluorinated hydrotropic co-surfactant of 3-6 carbons.

19. The thermodynamically-stable aqueous microemulsion of claim 18 wherein the fluorinated hydrotropic co-sufactant is a carboxylic acid, carboxylate or alcohol of 3-6 carbons.

* * * * *